United States Patent
Deangelo et al.

(10) Patent No.: US 8,336,365 B2
(45) Date of Patent: Dec. 25, 2012

(54) AUTOMATIC CALIBRATION ERROR DETECTION FOR ULTRASONIC INSPECTION DEVICES

(75) Inventors: Paul Joseph Deangelo, West Bridgewater, MA (US); Steven Abe Labreck, Boston, MA (US)

(73) Assignee: Olympus NDT Inc., Waltham, MA (US)

( * ) Notice: Subject to any disclaimer, the term of this patent is extended or adjusted under 35 U.S.C. 154(b) by 97 days.

(21) Appl. No.: 13/053,420

(22) Filed: Mar. 22, 2011

(65) Prior Publication Data

US 2011/0232360 A1     Sep. 29, 2011

Related U.S. Application Data

(60) Provisional application No. 61/317,446, filed on Mar. 25, 2010.

(51) Int. Cl.
*G01M 1/14* (2006.01)

(52) U.S. Cl. .......................................................... 73/1.86
(58) Field of Classification Search ........................ None
See application file for complete search history.

(56) References Cited

U.S. PATENT DOCUMENTS 6,122,968 A  *  9/2000  Vandervalk ..................... 73/642

* cited by examiner

*Primary Examiner* — Robert Raevis
(74) *Attorney, Agent, or Firm* — Ostrolenk Faber LLP

(57) ABSTRACT

Disclosed is a method and an NDT/NDI calibration process that automatically detects erroneous TOF readings by providing a predetermined time acceptance window. During the calibration process, TOF readings acquired by a UT device are validated to determine whether the TOF reading for the thin test block falls within the range of the predetermined time acceptance window. If the TOF reading for the thin block (T2) falls out of the predetermined time acceptance window, the operator is alerted of an error and to repeat the TOF test for the thin block.

8 Claims, 3 Drawing Sheets

AUTOMATIC CALIBRATION ERROR DETECTION FOR ULTRASONIC INSPECTION DEVICES

CROSS REFERENCE TO RELATED APPLICATIONS

This application claims priority under 35 U.S.C. §119(e) of U.S. Provisional Patent Application Ser. No. 61/317,446, filed Mar. 25, 2010, entitled "Automatic Calibration Error Detection for Ultrasonic Inspection Devices". The complete contents of the priority application are hereby incorporated by their reference for all purposes.

FIELD OF THE INVENTION

The present invention relates to non-destructive testing and inspection devices (NDT/NDI) and more particularly to a method that automatically detects calibration data errors for ultrasonic inspection systems, such as thickness gauge devices.

BACKGROUND OF THE INVENTION

Ultrasonic apparatus calibration procedures fall into three categories, namely Transducer Zero Compensation, Material Velocity Calibration and Zero Offset Calibration. Presently, "Two Point Calibrations", which is widely known in the art, utilizes the combination of "Zero Offset Calibration" and "Material Velocity Calibration."

"Two Point Calibration" for thickness measurement instruments typically involves the process of adjusting an ultrasonic inspection device (UT device) so that it takes measurement on known-thickness test objects for a particular material, using a particular transducer at a particular temperature. In most cases, Material Velocity and Zero Offset Calibration may be combined using a thick and a thin calibration block of the same material, which is referred to as "Two Point Calibration".

Material Velocity Calibration is typically performed using a thick test block of known thickness that is fabricated out of the same material to be measured, by measuring the time of flight of the ultrasonic signal that travels from the front surface to the back surface of the test material. This calibration needs to be completed for each batch of test objects.

Zero Offset Calibration is typically performed using a thin test block of known thickness made of the same material to be measured, by measuring the time of flight of the ultrasonic signal that travels from the front surface to the back surface of the test material. This calibration only needs to be performed once for each new transducer and material combination.

An existing conventional Two Point Calibration process for a given transducer typically involves the following steps:
1) Select a calibration block comprising a few sub-blocks with different but known thicknesses. Select two sub-blocks, with the thinner one called "thin block" and the thicker one called "thick block". The thicknesses of both thin block and thick block are known. The pertinent parameters of the transducer selected to be calibrated are either recalled from the UT device's memory or provided by the operator.
2) Determine T1, the measured time of flight (TOF) of the thick block, by using the UT device and the selected transducer. T1 is the TOF measured for the ultrasonic signal to travel from the front surface to the back surface and back to the front surface of the thick block.
3) Provide H1, the known thickness of the thick block, to the UT device.
4) Determine T2, the measured time of flight (TOF) of the thin block, by using the UT device and the selected transducer. T2 is the TOF measured for the ultrasonic signal to travel from the front surface to the back surface and back to the front surface of the thin block;
5) Provide 112, the known thickness of the thin block, to the UT device.
6) Lastly, the UT device performs the Two Point Calibration calculations and stores the results.

However, it is quite frequent that the UT device acquires an erroneous T2 for the thin block an account of factors such as incorrect gain or signal noise. The calibration would be therefore erroneous when an operator mistakenly accepts the erroneous T2. This has been problematic particularly for inexperienced operators who might unknowingly perform erroneous calibrations, which subsequently produce erroneous inspections. For experienced operators, erroneous readings slow down the calibration process, since the operator needs to stop and verify the calibration manually, which decreases productivity. Moreover, if there is not a waveform display on the UT device to view the signal during the calibration session, the operator has no means to determine if T2 is correct.

The accuracy of non-destructive testing (NDT) is well known to be critical for many industries.

Existing efforts are exemplified in U.S. Pat. No. 3,554,013 to Jerry Berg which deploys hardware circuitry to minimize the problems caused by erroneous calibration due to wrong signal detection. However, the hardware solution is comparatively not cost effective and adaptable and suffers from instability with thermal drift.

Thus, given the existing problems and tried efforts, there is a critical need to automatically remove erroneous calibration signals, especially for 'thin block' or "Zero Offset Calibration" to improve the inspection certainty, accuracy and to increase productivity.

SUMMARY OF THE INVENTION

The disclosure herein solves the problems related to the calibration of ultrasonic inspection devices used in NDT/NDI devices, where existing "Two Point Calibration" procedures typically encounter the aforementioned erroneous TOF readings, particularly for thinner blocks.

Note that the terms "probe", "transducer", and "sensor" used herein may be used interchangeably.

Time of Flight measurement is herein referred to as TOF, which is the time of flight measurement of the ultrasonic signal travelling from the front surface to the back surface and back to the front surface of either the thin or thick block.

The ultrasonic depth measuring apparatus is herein referred as the UT device.

Accordingly, it is a general object of the present disclosure to provide a method and an associated software procedure that may be employed to automatically determine if there is an error in detection of calibration signals during a "Two Point Calibration" process.

It is further an object of the present disclosure to carry out a Two Point Calibration with automatic erroneous signal detection according to the present invention. The process involves taking readings of TOF, T1 and T2 of a thick block and a thin block with known thickness H1 and H2, respectively, with the TOF reading for the thin block T2 verified for error before proceeding to calibrating the UT device.

It is further an object of the present disclosure to define a time acceptance window for the TOF reading for the thin block during the Two-Point Calibration process.

It is further an object of the present disclosure to validate whether the TOF reading for the thin block (T2) falls within the range of the predetermined time acceptance window. If the TOF reading for the thin block (T2) falls out of the predetermined time acceptance window, the operator is alerted for an error and to repeat the TOF of the thin block.

It also can be understood that the presently disclosed method for automatic calibration error detection provides the advantanges of improving calibration and therefore measurement/inspection confidence, accuracy and avoids erroneous readings.

It also can be understood that the presently disclosed method for automatic calibration error detection provides the advantanges of improving the calibrating productivity by eliminating time wasted in guessing whether the readings are valid, particularly if the UT device does not have a waveform display to verify (T2).

BRIEF DESCRIPTION OF THE DRAWINGS

FIGS. 1a and 1b are collectively used to describe the principle used by the auto calibration error detection according to the present invention.

DETAILED DESCRIPTION OF PREFERRED EMBODIMENTS

As described in the Background of the Invention, during a typical Two Point Calibration procedure, a transducer selected for calibration is engaged with a thick and then a thin block with known thickness (H1 and H2 respectively). The transducer is triggered and ultrasonic echo signals are captured by the UT device. Typical waveforms are plotted in FIGS. 1a and 1b.

Figure 1A:
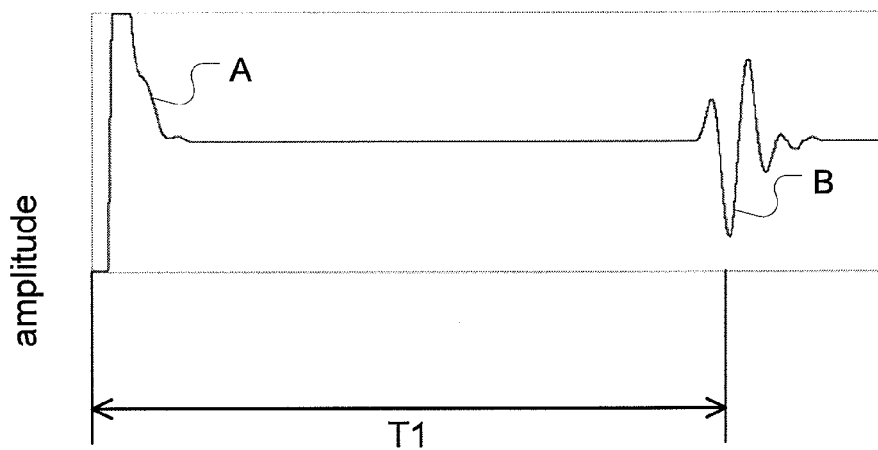
FIGS. 1a and 1b depict the ultrasonic waveforms reflected from the backwall boundary of the thick and thin block respectively.
Figure 1B:
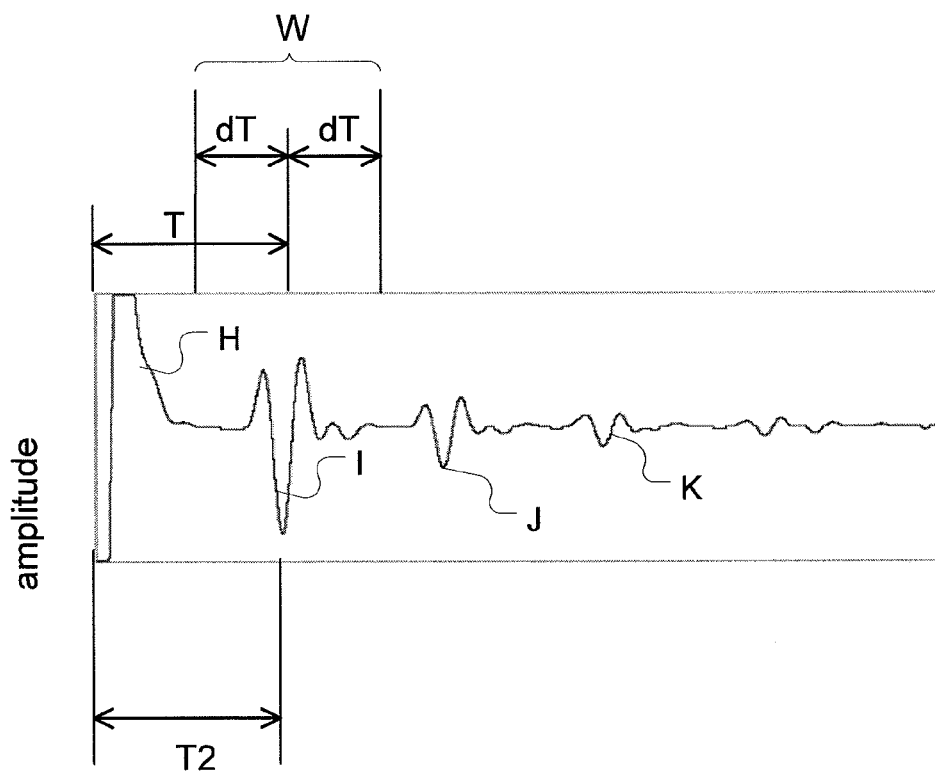

Referring to FIGS. 1a and 1b, the ultrasonic waveforms reflected from the thick and the thin blocks are shown respectively. For both FIGS. 1a and 1b, the X-axis depicts the time required for the ultrasonic signals to travel to and be reflected from the backwall boundary of the testing objects, namely the thick block and the thin block. The Y-axis is the ultrasonic echo signal amplitude detected by the UT device.

In FIG. 1a, A represents the excitation pulse of the ultrasonic signal. B represents the first echo signal from the bottom boundary of the thick block which is detected by the UT device. T1 is the TOF measurement of the first echo.

FIG. 1b shows the waveform of the detected echo signal when the calibration procedure is performed on the thin block. H is the excitation pulse of the ultrasonic signal. I is the first echo signal reflected from the back surface of the thin block which is detected by the UT device. Subsequently, J is the second echo signal and K is the third echo signal. T2 is the Time Of Flight measurement of the first echo I.

As can be noted in FIG. 1a, the first echo signal reflected from the back surface of the thick block is easily distinguishable, and there are no other major echos detected to confuse the echo reflected from the back surface.

However, for the case of the thin block, as shown in FIG. 1b, in addition to the first echo I reflected from the back surface of the thin block, there are other echoes (J and K) that could be easily confused with echo I. In existing practice, it often occurs that the UT Device misreads the TOF for echoes J or K, for the TOF of echo I.

In accordance with one novel aspect of the present invention, a predetermined time acceptance window is provided, where a correct reading of the TOF for the first echo is expected to fall. As shown in FIG. 1b, the time acceptance window, herein referred to as W is given based on a calculated thin block thickness T using the three known values of T1, H1 and H2. The details for such calculation are given later in the description associated with FIG. 3.

Also shown in FIG. 1b, dT is a predetermined tolerated window size. W is the time acceptance window.

If the echo TOF reading falls out of W, the UT device automatically aborts the reading and alerts the operator to repeat the TOF for the thin block.

Figure 2:
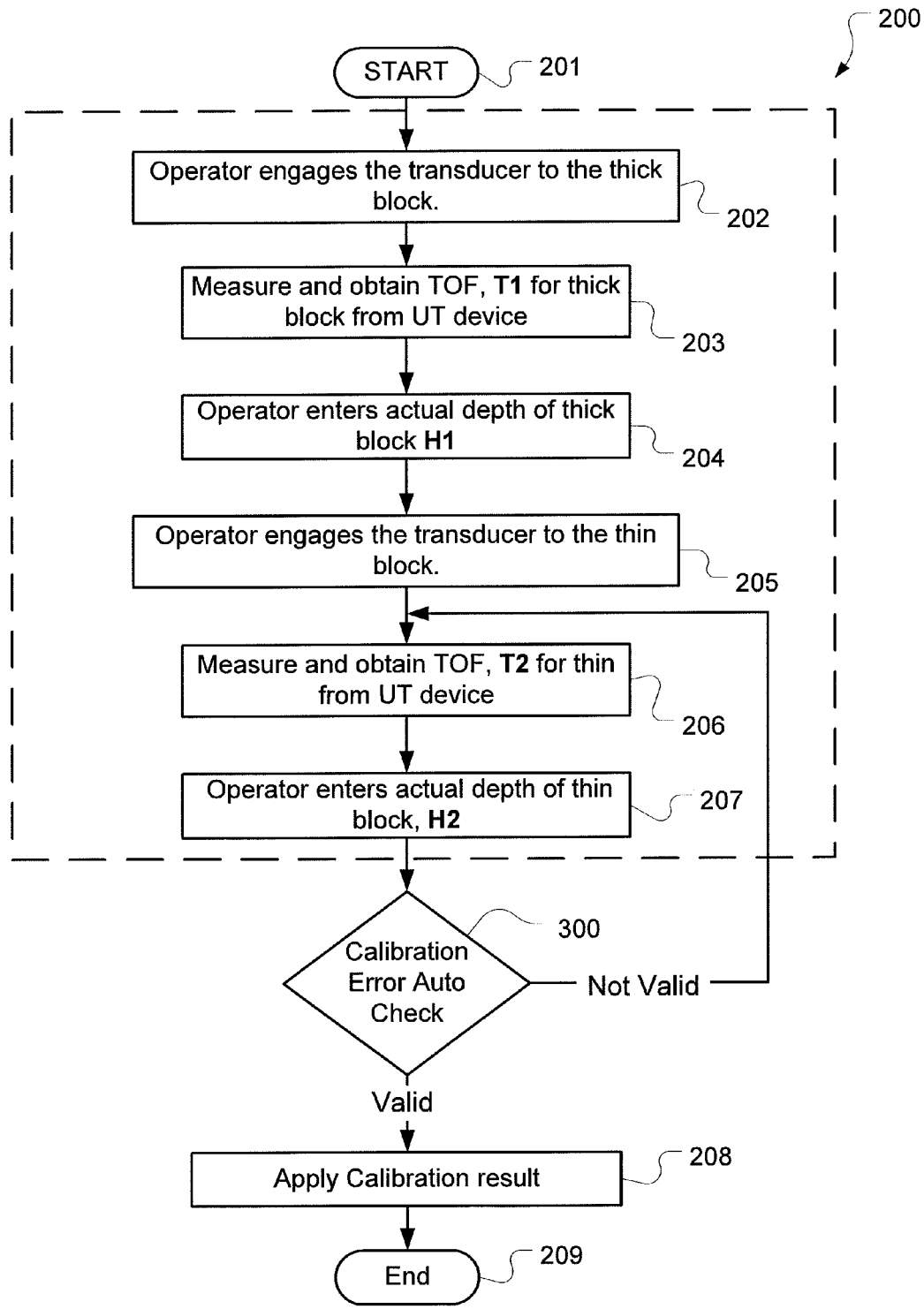
FIG. 2 is a flow chart of a procedure for Two Point Calibration with automatic error detection according to the present invention.

Reference is now made to FIG. 2, which is a flow chart depicting the procedure of two point calibration with the auto error detection according the present invention.

The calibration procedure is started at step 201. At step 202, the transducer selected for calibration is engaged to the thick block of the calibration. At step 203, TOF for the thick block, T1, is measured by the UT device. The actual known thickness of the thick block H1 is then provided to the UT device at step 204. The acquired ultrasonic waveform and T1 are shown in FIG. 1a.

Continuing with FIG. 2, at step 205, the transducer is engaged with the thin calibration block. At step 206, TOF for the thin block T2 is measured by the UT device. At step 207, the actual known thickness of the thin block H2 is then provided. The ultrasonic waveform and T2 are shown in FIG. 1b.

It should be noted that steps 201 through 207, together as steps 200, constitute the procedure of how an existing conventional Two Point Calibration is carried out.

Continuing with FIG. 2, after obtaining the TOF reading of the thin block, an aspect of the invention herein includes the check step 300 for the UT device to automatically verify if T2 falls within the predetermined valid range of W as shown in FIG. 1b. If T2 falls within W, the UT device applies the calibration result at step 208. If T2 falls outside of range W, the UT device issues a warning to the operator, alerting the operator to the need to adjust the gain of the UT device or verify other factors and retake the T2 measurement for the thin block by going back to step 206. The check step 300 is further elaborated in the following FIG. 3.

Figure 3:
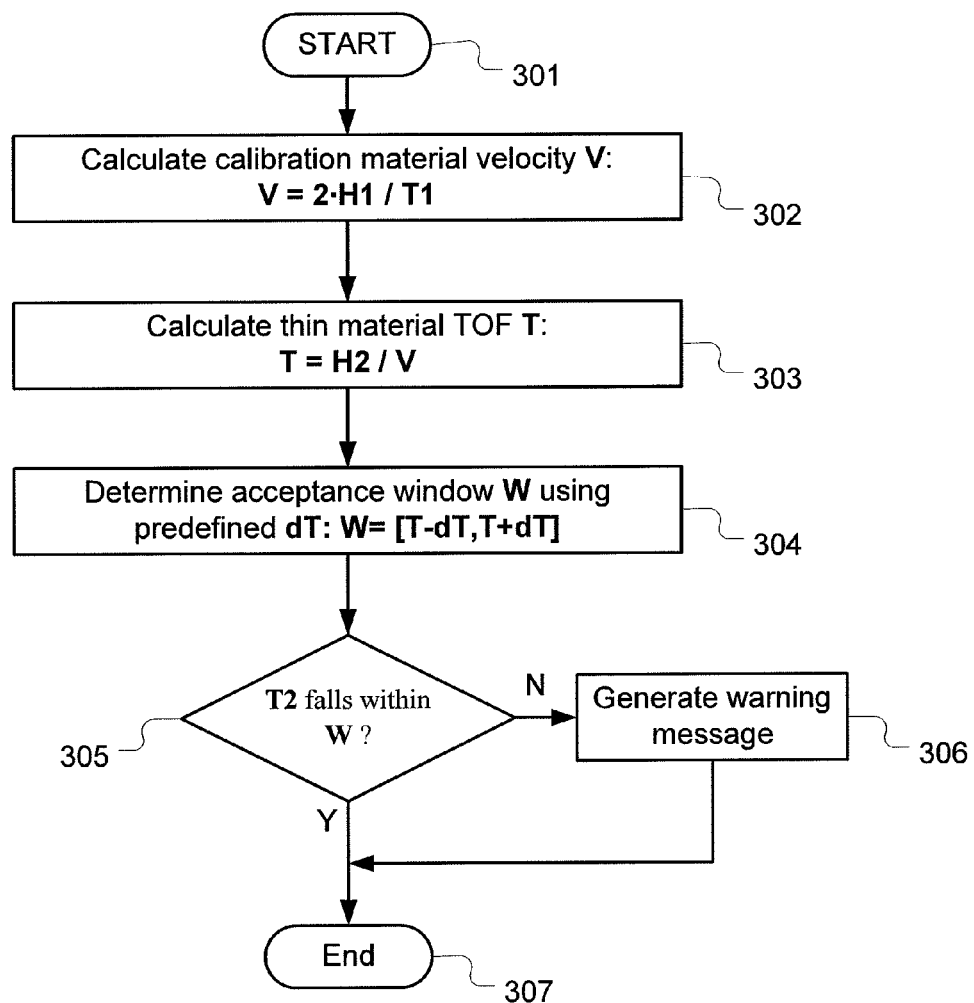
FIG. 3 is a flow chart showing the detailed procedure identifying erroneous readings outside of a predetermined window according to the present invention.

Referring now to FIG. 3, also referring back to FIG. 1b, the detailed process of the automatic T2 signal error detection is described. During this automatic T2 error detection process, the acceptance window W as defined in FIG. 1b and the validity of the TOF for the thin block T2 using the acceptance window W is determined.

At step 301, the signal error detection procedure is started. At step 302, calibration material velocity V is calculated using H1 and T1 according to $V = 2 \cdot H1/T1$. H1 and T1 are obtained in steps 202 and 203 in FIG. 2.

At step 303, the thin block TOF value T is calculated using H2 and V according to the equation $T = H2/V$. Then the TOF measurement detection window W is set using the predetermined dT at step 304 according to $W = [T-dT, T+dT]$. The value of dT is preferably given in a range of 30%-80% of value T.

At step 305, and as shown in FIG. 1b, the measured TOF of the thin block, T2, is verified using the acceptance window W.

If T2 is within this window W, the error detection procedure 300 is ended at step 307. At this point a valid T2 is provided and is used for the calibration procedure for the material velocity and zero offset in step 208.

If T2 does not fall within this acceptance window W, a warning message is generated at step 306, which prompts the operator to repeat the calibration reading for T2 as shown in FIG. 2.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to acoustic single element, multi-element, and array probes.

What is claimed is:

1. A method for calibrating an ultrasonic testing device comprising:
    providing a first test block formed of a material type to be tested, the first test block having a first thickness, and a second test block formed of the material type to be tested, the second test block having a second thickness less than the first thickness;
    measuring a first time-of-flight (TOF) of an ultrasonic excitation signal applied to the first test block by the ultrasonic testing device to be calibrated;
    calculating a predicted second TOF of an ultrasonic excitation signal applied to the second test block based upon the first TOF, the first thickness and the second thickness;
    measuring a second TOF of an ultrasonic excitation signal applied to the second test block by the ultrasonic testing device to be calibrated; and
    rejecting the second TOF measurement if it deviates from the predicted second TOF by more than a predetermined tolerated window size.

2. The method according to claim 1, wherein the predetermined tolerated window size comprises +/− about 30% to about 80% of the predicted second TOF.

3. The method according to claim 1, further comprising calculating the calibration material velocity as twice the first thickness divided by the measured first TOF.

4. The method according to claim 3, wherein the predicted second TOF is calculated as the second thickness divided by the calibration material velocity.

5. The method according to claim 1, wherein the predicted second TOF is proportional to the measured first TOF and proportional to the ratio of the second thickness to the first thickness.

6. The method according to claim 1, further comprising generating a warning message responsive to a rejection of the second TOF measurement.

7. The method according to claim 1, further comprising repeating the second TOF measurement responsive to a rejection of a second TOF measurement.

8. The method according to claim 1, further comprising applying the calibration result based upon the measured first and second TOF values to the ultrasonic testing device to be calibrated responsive to an acceptance of the second TOF measurement as within the predetermined tolerated window size.

* * * * *